United States Patent [19]
Nagel et al.

[11] Patent Number: 5,543,558
[45] Date of Patent: Aug. 6, 1996

[54] METHOD FOR PRODUCING UNSATURATED ORGANICS FROM ORGANIC-CONTAINING FEEDS

[75] Inventors: Christopher J. Nagel, Wayland, Mass.; Robert D. Bach, Gross Pointe, Mich.

[73] Assignee: Molten Metal Technology, Inc., Waltham, Mass.

[21] Appl. No.: 173,362

[22] Filed: Dec. 23, 1993

[51] Int. Cl.$^6$ .............................. C07C 67/30; C07C 1/00
[52] U.S. Cl. ............................................. 560/214; 585/241
[58] Field of Search ..................................... 560/211, 214

[56] References Cited

U.S. PATENT DOCUMENTS

| | | | |
|---|---|---|---|
| 2,858,255 | 10/1958 | Segui et al. | 202/219 |
| 3,974,206 | 8/1976 | Tatsumi et al. | 260/486 |
| 3,996,022 | 12/1976 | Larsen | 44/1 |
| 4,012,457 | 3/1977 | Bredeson et al. | 260/683 |
| 4,552,667 | 11/1985 | Shultz | 210/757 |
| 4,574,038 | 3/1986 | Wan | 204/162 |
| 4,574,714 | 5/1986 | Bach et al. | 110/346 |
| 4,666,696 | 5/1987 | Shultz | 423/659 |
| 4,769,507 | 9/1988 | Murib et al. | 585/500 |
| 5,177,304 | 1/1993 | Nagel | 588/201 |
| 5,191,154 | 3/1993 | Nagel | 588/201 |

FOREIGN PATENT DOCUMENTS

| | | |
|---|---|---|
| 0067491A2 | 12/1982 | European Pat. Off. . |
| 1618182 | 12/1970 | Germany . |
| 2058553 | 2/1974 | Germany . |
| 44-11648 | 5/1969 | Japan . |
| 936899 | 9/1963 | United Kingdom . |
| 1270074 | 4/1972 | United Kingdom . |
| 1350612 | 4/1974 | United Kingdom . |
| 2088893 | 6/1982 | United Kingdom . |
| 399526 | 9/1993 | United Kingdom . |
| 93/02751 | 2/1993 | WIPO . |

OTHER PUBLICATIONS

Chemical Abstract 76:18292 1971.
Chemical Abstract 78:158657 1972.
Chemical Abstract 86:55085 1977.
Adams et al., "Dehydrogenation and Coupling Reactions in the Presence of Iodine and Molten Salt Hydrogen Iodide Acceptors," *Journal of Organic Chemistry*, 42, No. 1:1–6, (1977).
Kashiwadate, et al., "The Dehydrogenation of Butyl Alcohols by the Molten–metal Catalysts," *Bulletin of the Chemical Society of Japan*, vol. 44, No. 11:3004–3009 (1971).
Saito et al., "Dehydrogenation of Some Alcohols by the Molten Metal Catalysts," *Bulletin of Japan Petroleum Institute*, 14, No. 2:169–173, (1972).
Haggin, J., "Growth and Dissociation of Metal–Carbon Nanocrystals Probed," *Chem. & Eng. News*, pp. 29–32, Oct. 25, 1993.
Haggin, J., "European Conference Draws Attention to Fundamental Role of Catalysts," *Chem & Eng. News*, pp. 26–30, Oct. 18, 1993.
Layman, P. L., "Advances in Feedstock Recycling Offer Help with Plastic Waste," *Chem & Eng. News*, pp. 11–14, Oct. 4, 1993.
Satterfield, C. N., "Acid and Zeolite Catalysts," In Gail F. Nalven (Ed.), *Heterogeneous Catalysts in Industrial Practice*, 2nd Ed., (NY: McGraw–Hill), pp. 209–266, pp. 339–417, (1991).
Jebens, A. M., "CEH Marketing Research Report, Ethylene," *Chemical Economics Handbook–SRI International*, (Report Olefins 432.0000 A) Sep., 1992.

*Primary Examiner*—Paul J. Killos
*Attorney, Agent, or Firm*—Hamilton, Brook, Smith & Reynolds, P.C.

[57] ABSTRACT

A method includes producing an unsaturated organic compound from an organic component of an organic-containing feed. A reactor is provided which contains a molten metal bath. The molten metal bath includes a metal, such as a suitable transition metal, which can interact with an organic component of the feed. The feed is directed into the molten metal bath at a rate which causes the metal to interact with the organic component. Operating conditions are established and maintained in the reactor to cause the metal to interact with the organic component. At least one carbon-carbon double bond is formed in the organic component to produce an unsaturated organic compound that is discharged from the molten metal bath.

72 Claims, 2 Drawing Sheets

METHOD FOR PRODUCING UNSATURATED ORGANICS FROM ORGANIC-CONTAINING FEEDS

BACKGROUND OF THE INVENTION

Considerable research has been conducted recently in the area of producing alkenes for use as industrial raw materials. Among the many uses of such commodity chemicals include plastic and fibers for consumption in packaging, transportation and construction industries. Of particular interest are areas of research focusing on production of alkenes, such as ethylene, which is consumed principally in the manufacture of polyethylene, and substituted alkenes, such as ethylene dichloride and vinyl chloride. Ethylene is also employed in the production of ethylene oxide, ethyl benzene, ethylene dichloride, ethylene-propylene elastomers and vinyl acetate.

The primary sources of alkenes, such as ethylene, include: steam cracking of organics, such as gas oils; off-gas from fluid catalytic cracking (FCC) in oil refineries, catalytic dehydration of alcohols; and recovery from coal-derived synthesis gas. However, the worldwide demand for alkenes is extraordinary: the short fall in worldwide supply of ethylene alone was estimated in 1991 to be about 2.3 million tons, as determined by the Chemical Economics Handbook, SRI International (1992). Further, known methods for producing alkenes have significant drawbacks. For example, organic steam cracking, which accounts for about 100% of ethylene production in the U.S., is a mature technology which is highly sensitive to process variables, such as cracking severity, residence time and hydrocarbon partial pressure, as well as plant economics and price fluctuation. Other methods, such as alkene cracking over a solid support, can cause "coking up," which requires frequent burnout of the solid support to continue processing. In addition, such processes are facing increasing environmental regulatory pressure to control systemic problems, such as leaks and failure from related equipment and safety concerns associated with alkene cracking.

Other listed production methods have even greater limitations. The availability of FCC off-gas, for example, generally prohibits its use as an economically viable feed stock. Catalytic dehydration of alcohols is effectively limited to certain countries that have large amounts of readily available fermentation raw material. Also, known methods for production of alkenes from other sources, such as coal and coal-derived naphtha and methanol are, at best, only marginally commercially viable.

Further, Government pressure to recycle plastic materials is increasing due to the more than two billion pounds of packaging plastics that are introduced into the market each year. However, the potential significance of recycling plastic into feedstocks, syncrude oils or monomers is hampered by costs that are typically higher than those of other ways of dealing with plastic waste. Incineration with energy recovery is the method that industry generally prefers. Although recycling postconsumer waste is highly desirable, typical plastic containing wastes do not meet the criteria for feasibility of existing processes. For example, collection methods are variable and the waste often needs to be cleaned or preprocessed in some fashion that adds to the recycling cost.

Using chemolysis methods of depolymerizing single condensation polymers, such as polyethylene terephthalate (PET), nylon and polymethyl methacrylates (PMMA), is theoretically possible, but the difficulty is in handling mixed plastics. Bulk thermoplastics that are present in mixed plastics can generally be broken down only by thermal cracking to naphthalene feed stock. Other technologies include gasification of plastics with coal sources, oxygen and steam to produce synthesis gas. Coal liquefaction methods can also produce a syncrude oil from mixed plastics.

Therefore, a need exists for an improved method of producing alkenes which significantly reduces or eliminates the above-mentioned problems.

SUMMARY OF THE INVENTION

The invention relates to a method for producing an unsaturated organic compound from an organic component of an organic feed.

The method includes providing a reactor containing a molten metal bath. The molten metal bath includes a metal which can interact with an organic component of the feed. The feed is directed into the molten metal bath at a rate which causes the metal to interact with the organic component. Operating conditions are established and maintained in the reactor to cause the metal to be eliminated from at least a portion of the organic component, whereby at least one carbon-carbon double bond is formed in that portion of the organic component to produce an unsaturated organic compound that is discharged from the molten metal bath.

The present invention includes many advantages. For example, the present invention provides good control over production of organics such as alkenes including ethylene. Also, improved yields of ethylene are obtained by the present invention. The present method is a homogenous catalytic recycling process, employing solution equilibria to synthesize commercial products, such as methane, ethane and propane, from a wide variety of organic feeds, including hazardous industrialized wastes. The present invention also has the ability to sustain high product quality with varying feed heterogeneity, including chemical or physical complexity. In addition, the invention provides flexibility to engineer the properties and composition of a ceramic phase generated by the method. Further, the present invention has the ability to recover and recycle volatile and nonvolatile metals.

A need exists for a technology that is robust enough to handle complex organic mixtures, such as plastic wastes that are also contaminated with glass, paper and metals, etc., and which can produce resalable commodity chemicals or chemical intermediates. What the polymer chemist has joined into high molecular weight plastic materials, this invention can split asunder.

The invention offers advantages over existing technologies in that glass contaminants will dissolve and accrue to the ceramic layer. Those metal contaminants that have free energies of oxidation greater than that of carbon will be converted in the presence of oxygen to bath-insoluble metal oxides and accumulate in the ceramic layer. Other metals will either remain in the molten metal bath or volatilize and be collected in a known manner. Carbon-containing materials can dissolve in the bath and combine with a portion of the spurious oxygen or oxygen introduced as part of mixed plastic materials can form heat liberating carbon monoxide and then escape the bath. Plastic materials containing aromatic substituents such as PET can be partially cleaved to produce aromatic compounds such as benzene that can be removed and collected as a synthetic intermediate. Polyethylene plastics can be cleaved by oxidative addition-reductive elimination to produce ethylene and related alkenes. Polypropylene can be induced to revert back to propylene in a similar fashion. Polymeric materials such as PMMA can undergo C—C bond rupture to produce methyl methacrylate monomer and lower molecular weight fragments upon the loss of $CO_2$.

DETAILED DESCRIPTION OF THE INVENTION

The features and other details of the method of the invention will now be more particularly described with reference to the accompanying figures and pointed out in the claims. It will be understood that particular embodiments of the invention are shown by way of illustration and not as limitations of the invention. The principal functions of this invention can be employed in various embodiments without departing from the scope of the invention.

The present invention generally relates to a method for producing an unsaturated organic compound from an organic component of a feed. The organic component can be a component of a waste stream fed to the bath of molten metal. Processes for decomposing waste in molten metal baths are disclosed in U.S. Pat. Nos. 4,574,714, 5,177,304, and 4,602,574 which are incorporated herein by reference.

Figure 1:
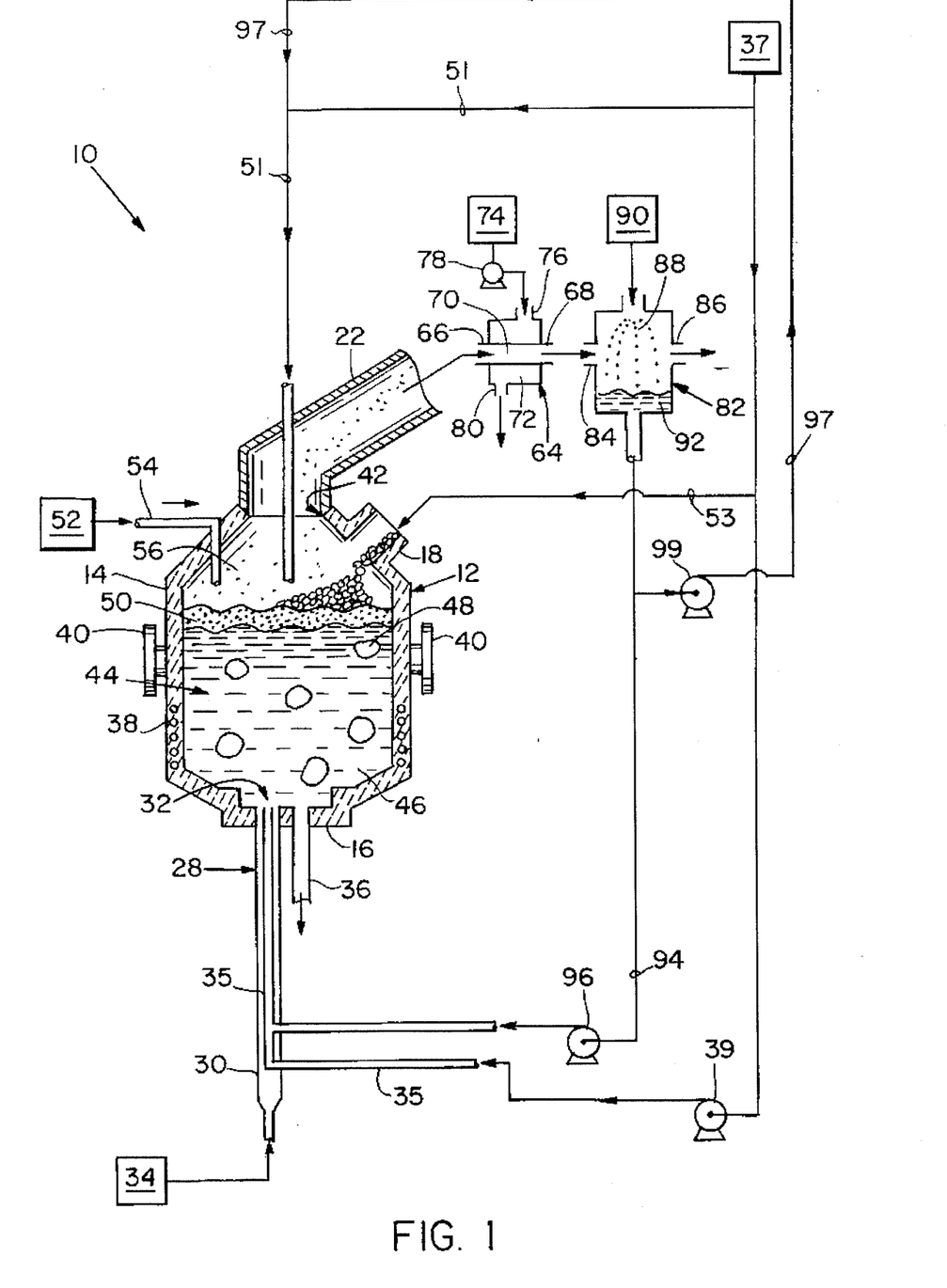
FIG. 1 is a schematic representation of one embodiment of apparatus suitable for conducting the method of the invention.

In one embodiment of the invention, illustrated in the Figure, system 10 includes reactor 12. Examples of suitable vessels include those described in U.S. Ser. No. 08/041,490 and U.S. Ser. No. 08/041,405, the teachings of which are incorporated herein by reference and reactors which are described in U.S. Pat. Nos. 4,574,714, 5,177,304, and 4,602,574. Reactor 12 has an upper portion 14 and a lower portion 16. Feed inlet 18 at upper portion 14 of reactor 12 is suitable for directing feed into reactor 12. Off-gas outlet 22 extends from upper portion 14 and is suitable for conducting an off-gas out of reactor 12.

It is to be understood that the feed stream is generally introduced to molten metal bath 44 without injection of a coolant if reaction of the feed in reactor 12 is endothermic. However, tuyere 28 is dimensioned and configured for conjointly and continuously introducing a suitable feed stream and coolant into reactor 12. Tuyere 28 includes coolant tube 30 and feed inlet tube 35. Coolant tube 30 extends from coolant source 34 to reactor 12. Feed inlet tube 35 extends from feed source 37 to tuyere 28. Feed inlet tube 35 is disposed at tuyere opening 32. Pump 39 is disposed at tuyere 28 to direct a suitable feed stream from feed source 37 and through tuyere opening 32 into reactor 12. It is to be understood that an oxidant can also be fed to reactor 12 through tuyere 28 and/or at other locations within reactor 12, as are taught in U.S. Pat. No. 5,191,154, the teachings of which are incorporated by reference.

It is also to be understood that more than one tuyere 28 can be disposed in reactor 12 and that concentric, or multiple concentric tuyeres, can be employed for separate introduction of the feed stream into reactor 12. Further, it is to be understood that feed can be introduced into reactor 12 by other suitable methods, such as by employing a lance, etc.

Bottom-tapping spout 36 extends from lower portion 16 and is suitable for removal of at least a portion of a molten bath from reactor 12. Additional drains can be provided as a means of continuously or intermittently removing distinct molten phases. Material can also be removed by other methods, such as are known in the art. For example, material can be removed from reactor 12 by rotating vessel 12 and employing a launder, not shown, extending from feed inlet 18. Alternatively, the launder can extend into reactor 12 through a tap hole, also not shown.

Induction coil 38 is disposed at lower portion 16 for heating reactor 12 or for initiating generation of heat within reactor 12. It is to be understood that, alternatively, reactor 12 can be heated by other suitable means, such as by plasma torch, electric arc, etc. Trunions 40 are disposed at reactor 12 for manipulation of reactor 12. Seal 42 is disposed between reactor 12 and off-gas outlet 22 and is suitable for allowing partial rotation of reactor 12 about trunions 40 without breaking seal 42. Alternatively, reactor 12 does not include trunions 40 or seal 42 and does not rotate.

Molten metal bath 44 is disposed within reactor 12. In one embodiment, molten metal bath 44 includes a metal which, when molten, causes at least a portion of saturated hydrocarbon in the injected feed to be reformed to at least one unsaturated alkene, such as ethylene, under the operating conditions of system 10. In one embodiment, the metals of molten metal bath 44 have a melting point in the range of between about 900° C. and 1,100° C. The melting point of bath 44 is low enough to cause the organic components of the injected feed to be reformed, and subsequently discharged from bath 44, at least one unsaturated organic compound of lower molecular weight.

In a particularly preferred embodiment, the operating conditions of the bath include, for example, temperatures which prevent substantial degradation of organic compounds. Also, the required residence times of the feed in the bath of molten metal are substantially shorter than are those typically employed to thermally decompose organic-containing feeds.

The thermal history of the organic compounds in the reaction zone is affected by the reaction zone temperature, residence time of the compounds in the reaction zone, and various intensive properties associated with materials in the reaction zone. The effective operating temperature is that temperature to which organic species of interest are exposed while they are in the reaction zone. This temperature is chosen so as to maximize the conditions which lead to product formation while minimizing any subsequent product degradation reactions. The effective temperature can be achieved under conditions supporting thermal equilibrium (e.g., having low temperatures in the reaction zone and relatively long residence times) or under conditions that prevent thermal equilibrium (e.g., very high temperatures in the reaction zone with relatively short residence times). For example, if the optimal product formation occurs at a substrate temperature of 900° C., this could be achieved with a liquid metal operating at 900° C. and allowing sufficient residence time for the product to reach thermal equilibrium or it could be achieved by injecting it into a high temperature reaction zone (e.g., 2000° C.) for a very short period of time, thereby providing insufficient time for the product to reach thermal equilibrium (i.e., allowing the product to exit the reaction zone at 900° C.). "Thermal equilibrium," as defined herein, means the temperature with the reaction zone is substantially uniform. Generally, the residue time of feed components with the reaction time is less than about five seconds. In one embodiment, the residence time is less than about 0.1 seconds.

Examples of suitable metals in molten metal bath 44 include transition metals and, in particular, transition metals which have an energy gap between their ground and first excited electronic states of less than about 1.5 eV. Examples of especially suitable transition metals include rhodium and alloys including at least one suitable metal component. It is to be understood that molten metal bath 44 can include oxides of the molten metals. As disclosed in U.S. Pat. No. 5,177,304, the teachings of which are incorporated herein, molten metal bath 44 can include more than one phase of molten metal. In another embodiment, the ceramic phase can include at least one salt. Alternatively, a substantial portion of molten metal bath 44 can be of elemental metal.

Molten metal bath 44 can be formed by at least partially filling reactor 12 with a suitable metal. The metal is then heated to a suitable temperature by activating induction coil 38 or by other means, not shown. Optionally, two immiscible metals can be introduced to reactor 12, whereby the metals separate during melting to form two distinct molten metal phases. In one embodiment, the viscosity of at least one phase of molten metal bath 44 is less than about ten centipoise at the operating conditions of system 10. In another embodiment, the viscosity of at least one phase of molten metal bath 44 is less than about thirty poise at the operating conditions of system 10.

Ceramic layer 50 is disposed on molten metal bath 44. Ceramic layer 50 is substantially immiscible with molten metal bath 44. Alternatively, system 10 does not include ceramic layer 50. The solubility of carbon in ceramic layer 50 can be less than that of molten metal bath 44, thereby causing atomic carbon to be retained within molten metal bath 44. In another embodiment, ceramic layer 50 has a lower thermal conductivity than that of molten metal bath 44. Radiant loss of heat from molten metal bath 44 can thereby be reduced to significantly below the radiant heat loss from molten metal bath 44 when no ceramic layer 50 is present.

Examples of suitable metal oxides of ceramic layer 50 include titanium oxide ($TiO_2$), zirconium oxide ($ZrO_2$), aluminum oxide ($Al_2O_3$), magnesium oxide (MgO), calcium oxide (CaO), silica ($SiO_2$), etc. Other examples of suitable components of ceramic layer 50 include halogens, sulfur, phosphorus, heavy metals, etc. It is to be understood that ceramic layer 50 can include more than one metal oxide. Ceramic layer 50 can contain more than one phase. Typically, ceramic layer 50 is substantially fluid, thereby allowing gases to pass across ceramic layer 50 from molten metal bath 44.

Ceramic layer 50 can be formed by directing suitable materials, such as metals, metal oxides, halogens, sulfur, phosphorus, heavy metals, sludges, etc., from source 52 through inlet tube 54 and into molten metal bath 44. The materials from source 52 can be directed onto the top of molten metal bath 44 or injected into molten metal bath 44, using methods such as are well-known in the art. The materials can form other stable compounds at the operating conditions of system 10 by reaction, for example, with alkali metal cations or alkaline earth metal cations. Examples of such stable reaction products include calcium fluoride ($CaF_2$) and magnesium phosphate ($Mg(PO_4)_2$). In one embodiment, ceramic layer 50 contains about forty percent calcium oxide, about forty percent silicon dioxide, and about twenty percent aluminum oxide, and is about five inches thick.

Feed, such as an organic-containing waste in solid, liquid, or gaseous form, is directed from feed source 37 into a reaction zone within reactor 12. The reaction zone is defined to be the region in which the production formation reaction(s) occur. It can include the volume within the reactor and within subsequent off-gas handling equipment. The conditions supporting reaction includes the liquid metal system, the gas/liquid interface, and the gas space above the liquid metal which contains metal vapor and reactive metal particles and droplets (caused by entrainment).

The feed can be introduced to reactor through line 35, line 51 and/or line 53. The feed includes at least one organic component. Examples of suitable organic components include alkyl and aryl substituents, and alkyl and aryl organic compounds bearing alkyl and aryl substituents. Specific examples of suitable organic components include methane, n-hexane, polyethylene, polyvinyl chloride, polyethylene terephthalate, nylon, polymethyl methacrylates, and mixed plastics. Examples of suitable feeds include "dirty" crude oil, bottoms from refineries, oil shales, hazardous wastes, waste plastics, including nylon and polymethyl methacrylate, etc.

In one embodiment, the feed is injected into molten metal bath 44 as a component of a feed stream that also includes an inert gas component, such as argon. In one example, the feed stream can be formed by vaporizing liquid organic feed in the presence of an inert gas. The amount of volatilized feed component in the feed stream can be, for example, in the range of between about five and forty percent, by volume.

In addition, the organic component of the feed stream can also include other atomic constituents, such as halides, metals, etc. Metal components in the feed stream can include metals, such as transition metals, which can interact with the organic component of the feed stream to form the organometallic intermediate. Also, a metal component of bath 44 can be a metal anion formed by reduction in metal bath 44 of a metal component of the organic feed. The metal component can be reduced by a metal component of bath 44.

The feed stream directed into reactor 12 combines with molten metal bath 44 and can also combine with ceramic layer 50. The feed stream and coolant are directed into molten metal bath 44 through tuyere 28. The feed stream can also be directed into reactor 16 from feed source 37 through conduit 51. Conduit 51 discharges the feed beneath the surface of molten metal bath 44. Contact of the feed with molten metal bath 44 or ceramic layer 50 exposes the feed to conditions sufficient to form an unsaturated organic product.

Consistent with the reaction zone definition, the reaction can be carried out predominantly in the liquid metal phase, the space immediately above the condensed liquid metal phase, or in the gas space above the condensed reaction media bath, provided that sufficient concentrations of vapor, droplet, particle, etc., exist to support the necessary reaction rates. Optionally, at least a portion of molten metal bath 44 can be suspended by gas directed through tuyere 28. Suspended molten metal bath 44 can be a continuum of metal extending through a generally gaseous volume, or a region of particulate molten metal suspended in a generally gaseous volume within reactor 12.

It is believed that, in one viable pathway for alkene formation, the metal component of molten bath 44 inserts into a sigma bond of the organic feed components, which affords transient organometallic intermediate where the metal is formally oxidized with the resultant formation of two sigma bonds, as shown below:

The energetic requirements for this type of insertion is about thermoneutral because the sum of the bond strengths of the two newly-formed sigma bonds is about equal to that of the sigma bond. This type of oxidative addition is facilitated by metals that have relatively low energy gaps between the ground state of the metal and its first excited state. Preferably, the energy gap is less than about 1.5 eV.

The metal is then eliminated from at least a portion of the organometallic intermediate, whereby at least one carbon-carbon double bond is formed in said organic compound. The organic component is thereby reformed to produce an unsaturated organic compound which is discharged from reactor 12 as a gas. For example, if the organic component of the feed is butane, oxidative addition, and subsequent elimination, of a suitable metal, such as rhodium, would cause the butane to be reformed into the unsaturated organic compound, butene. Continued exposure of butene to the rhodium would cause the butene to be oxidatively added to, and then eliminated from, the rhodium to form two ethylene molecules.

Suitable operating conditions of system 10 include a temperature sufficient to cause the feed and metal of molten metal bath 44 to interact and thereby form at least one transient organometallic intermediate. "Organometallic intermediate," as that term is used herein, means a compound or complex which is a product of a reaction or some other interaction between a metal and an organic component of a feed stream directed into molten metal bath 44. The metal of the organometallic intermediate can subsequently be eliminated from at least a portion of the organic component of the organometallic intermediate to cause the organic component to be reformed into an unsaturated organic compound.

Figure 2:
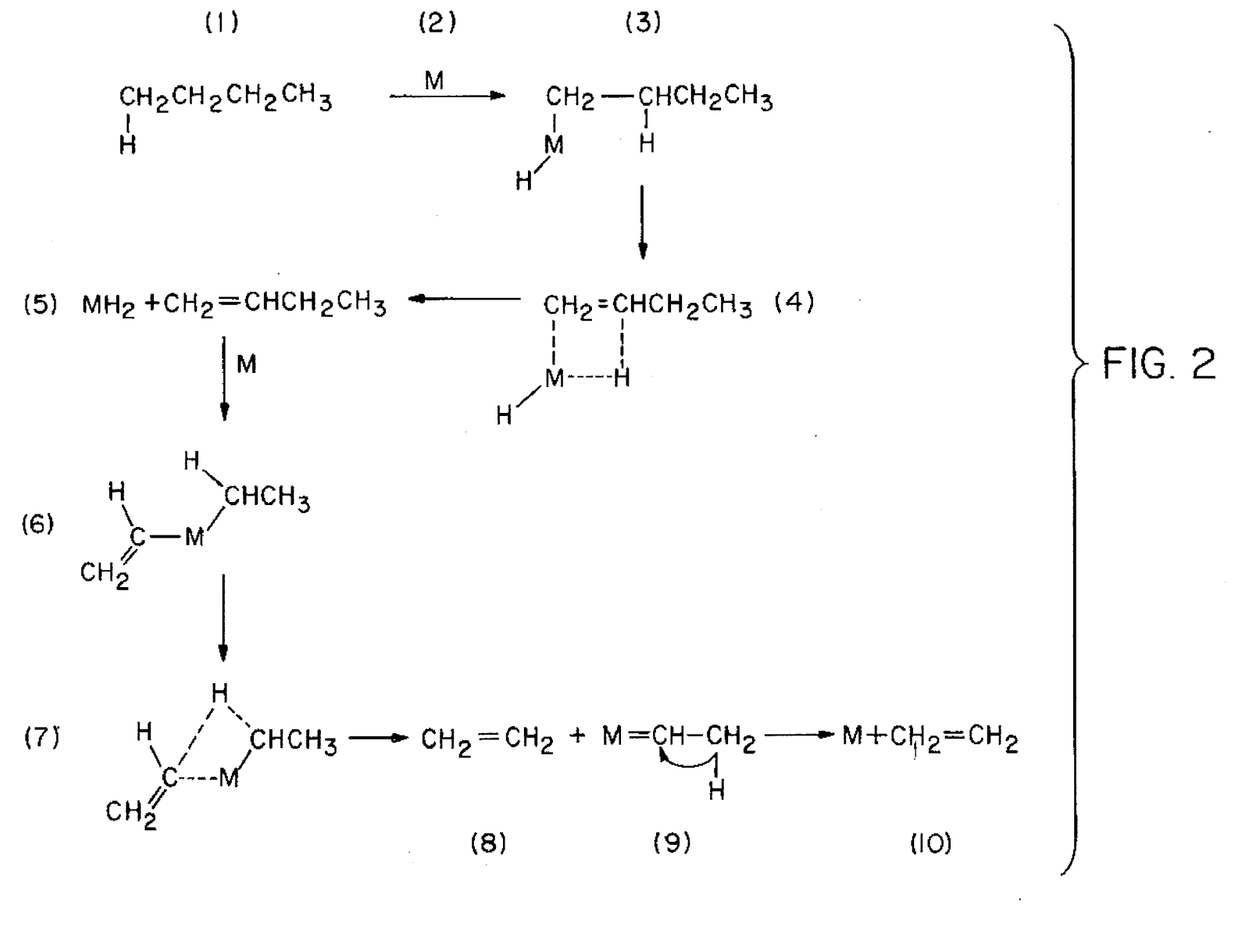
FIG. 2 is a representation of oxidative addition/reductive elimination for producing unsaturated organic compounds from organic-containing feeds according to the method of the present invention.

One possible pathway for metal substitution into the saturated organic component of a feed to form an organometallic intermediary and subsequent unsaturated organic compounds is shown by the reformation of butane to ethylene in FIG. 2. In this embodiment, introduction of butane (1) into a bath of molten metal M(2) causes oxidative addition, or substitution of metal M(2) into the butane(1), to form a organometallic intermediate(3). The metal causes a carbon-carbon double bond to form between carbons 1,2 of the metal-substituted butane(3). Subsequent β-elimination causes the metal to separate from the intermediate as a metal dihydride ($MH_2$) and thereby form 1-butene(5). Reductive elimination of $H_2$ from $MH_2$ regenerates the metal (2). Continued exposure of the organic compound causes the metal of the bath to be substituted between carbons 2,3 of the butylene to form a second organometallic intermediate(6). α-Elimination then causes reformation of second metallic intermediate(6) through a transition structure(7) to an ethylene(8) and a metallo-ethylidene complex(9). The complex is then converted to additional ethylene(10) by reductive elimination and hydrogen rearrangement. It is to be understood that the reaction pathway can be controlled and terminated at any intermediate stage by varying the operating conditions of the bath of molten metals.

In one embodiment, molten metal bath 44 has a low solubility limit for carbon under the operating conditions established and maintained by the method. As a consequence, incomplete dissociation and/or carbon dissolution can occur and the unsaturated organics are not converted to dissolved atomic constituents of carbon and hydrogen, but rather are reduced to shorter carbon chains prior to product-forming reactions. The carbon solubility in the molten metal is sufficient to provide the driving force necessary to initiate reformation and, can be less than 80% of the equilibrium solubility. The conditions of the bath which cause the reformation to form product include, for example, substantially reduced temperatures of the bath of molten metal, as compared to temperatures typically employed to thermally decompose organic materials or higher normalized feed rates. Thermal decomposition of organic components typically involves a homolytic bond rupture of a covalent sigma bond to form free radicals (i.e. R—R→2R). Also, the required residence times of the alkyl feed in the bath of molten metal are substantially shorter than are those known to cause complete monatomic dissolution of waste feeds.

If necessary, a coolant can be employed to cool tuyere 28. Examples of suitable coolants include steam, methane ($CH_4$), hydrogen gas ($H_2$), etc.

Gaseous layer 56 is formed over ceramic layer 50. In one embodiment, gaseous layer 56 extends from upper portion 14 of reactor 12 through off-gas outlet 22 to scrubber 82. A reaction zone within system 10 includes molten metal bath 44, ceramic layer 50 and gaseous layer 56. Reactants can be introduced anywhere within the reaction zone. Gaseous layer 56 includes off-gas formed in molten metal bath 44 and in ceramic layer 50. The off-gas includes reaction products, such as unsaturated organic formed in molten metal bath 44. The off-gas can also include at least one by-product which has been entrained or which has been volatilized before reformation to the unsaturated organic compound is complete.

Off-gas formed in reactor 12 is conducted from the reaction zone through off-gas outlet 22 to heat exchanger 64. Heat exchanger 64 can be any suitable heat exchanger for cooling off-gas discharged from reactor 12. Examples of suitable heat exchangers include water-cooled hoods, shell-and-tube heat exchangers, fluid beds, etc. Examples of off-gas components include unreacted or fragmented portions of the organic feed component.

The off-gas is conducted into heat exchanger 64 through heat exchanger off-gas inlet 66 and then through heat-exchanger off-gas outlet 68. Optionally, the off-gas is cooled in heat exchanger 64 by conducting the off-gas through an off-gas side 70 of heat exchanger 64 and by directing a suitable cooling medium through a medium-side 72 of heat exchanger 64. Examples of suitable cooling media include, for example, water, ethylene glycol, ethyl benzene, alcohols, etc. The cooling medium is directed from cooling medium source 74 through cooling medium inlet 76 of heat exchanger 64 by a suitable means, such as by use of pump 78 disposed between cooling medium source 74 and heat exchanger 64. The cooling medium is directed through the medium side 72 of heat exchanger 64, thereby cooling the off-gas, and then directed out of heat exchanger 64 through cooling medium outlet 80.

The off-gas is directed out of heat exchanger off-gas outlet 68 to a suitable separating means for exposing the off-gas to conditions sufficient to remove at least a portion of an intermediate component from the off-gas. In one illustration, the separating means is scrubber 82. The off-gas is directed through scrubber off-gas inlet 84 and then through scrubber 82 to scrubber off-gas outlet 86.

Scrubber fluid 88 is directed from scrubber fluid source 90 to scrubber 82 by a suitable means, such as by gravity or by a pump, not shown. Scrubber fluid 88 is introduced to scrubber 82 at a temperature suitable for removing at least a portion of the component from the off-gas.

It is to be understood that additional separating means can be employed to separate components from off-gas discharged from reactor 16. For example, a suitable cyclone separator, not shown, and a suitable spray drier, also not shown, can be disposed between heat exchanger 64 and scrubber 82.

Liquid composition 92 is formed by scrubbing of the off-gas with scrubber fluid 88. Liquid composition 92 is directed from scrubber 82 to reactor 12. In one embodiment, liquid composition 92 is pumped through piping 94 by pump 96 to the feed inlet tube 35. Examples of suitable pumps include a centrifugal pump, a positive displacement pump, etc. Liquid composition 92 is thereby combined with the feed for introduction into molten metal bath 44 through tuyere 28. In another embodiment, liquid composition 92 is directed through piping 97 by pump 99 to conduit 51. Liquid composition 92 is thereby combined with the feed stream for introduction into reactor 12 and onto molten metal bath 44.

At least a portion of the off-gas components are thereby returned in liquid composition 92 from the off-gas to molten metal bath 44. A substantial portion of the discharged feed components are then chemically reformed to unsaturated organic, such as ethylene. Chemical reaction of the feed components in system 10 is thereby controlled.

The invention will now be further and specifically described by the following examples. All parts and percentages are by weight unless otherwise stated.

EXAMPLE 1

A 20 lb. hot metal capacity unit was used for the experimental trials, with a susceptor/crucible arrangement used for containment and heating. Various organic liquids were fed and the production of unsaturated organics was monitored. Feed addition was achieved by vaporizing the organic and sweeping it with an inert gas to achieve the desired inlet concentration. The gas mixture was subsequently added to the reaction zone submerged into the condensed liquid media with steady state being achieved after 15 minutes. The results are summarized below.

TABLE 1

| | "Submerged" Addition | | | |
|---|---|---|---|---|
| Metal | Temperature °C. | Feed | Sample # | Ethylene Yield (%) |
| Tin Base | 900 | n-hexane | 21 | 17.9 |
| " | " | " | 22 | 17.7 |
| " | " | " | 27 | 16.5 |
| " | " | " | 31 | 17.0 |
| " | " | " | 35 | 16.0 |

The average residence time of feed components in the reaction zone was about 4.1 seconds.

EXAMPLE 2

A 20 lb. hot metal capacity unit was used for the experimental trials, with a susceptor/crucible arrangement used for containment and heating. Various organic liquids were fed and the production of unsaturated organics was monitored. Feed addition was achieved by vaporizing the organic and sweeping it with an inert gas to achieve the desired inlet concentration. The gas mixture was subsequently added to the reaction zone above the condensed reaction media with steady state being achieved after 15 minutes. The results are summarized below.

TABLE 2

| | "Non-Submerged" Addition | | | |
|---|---|---|---|---|
| Metal | Temperature °C. | Feed | Sample # | Ethylene Yield (%) |
| Tin Base | 900 | n-hexane | 12 | 13.8 |
| " | " | " | 13 | 13.6 |
| " | " | " | 14 | 13.4 |
| " | " | " | 15 | 13.0 |
| " | " | " | 16 | 13.5 |

The average residence time in the reaction zone was about 4.1 seconds.

EXAMPLE 3

A 20 lb. hot metal capacity unit was used for experimental trials, with a susceptor/crucible arrangement used for containment and heating. Various organic liquids were fed and the production of unsaturated organics was monitored. Feed addition was achieved by vaporizing the organic and sweeping it with an inert gas to achieve the desired inlet concentration. The gas mixture was subsequently added to the reaction zone and the neutral metal was varied to establish the impact on reaction performance. The average residence time of the feed components in the reaction zone in all cases was about 4.1 seconds. The results are summarized below.

TABLE 3A

| | Metal Efficiency | | | |
|---|---|---|---|---|
| Metal | Temperature °C. | Feed | Sample # | Ethylene Yield (%) |
| 100% Tin | 900 | n-hexane | 33 | 14.5 |
| " | " | " | 34 | 15.1 |
| " | " | " | 35 | 16.0 |
| 80% tin, 20% brass | 900 | n-hexane | 24 | 20.7 |
| " | " | " | 25 | 20.8 |
| " | " | " | 26 | 21.1 |
| " | " | " | 27 | 21.9 |

TABLE 3B

| | Metal Efficiency | | | |
|---|---|---|---|---|
| Metal | Temperature °C. | Feed | Sample # | Ethylene Concentration (%) |
| 100% Tin | 700 | n-hexane | 1 | 1.10 |
| " | " | " | 2 | 1.25 |
| " | " | " | 3 | 1.25 |
| 80% tin, 20% zinc | 700 | n-hexane | 1 | 0.74 |
| " | " | " | 2 | 0.75 |
| " | " | " | 3 | 0.64 |

A 20 lb. hot metal capacity unit was used for experimental trials, with a susceptor/crucible arrangement used for containment and heating. Various organic liquids were fed and the production of unsaturated organics was monitored. Feed addition was achieved by vaporizing the organic and sweeping it with an inert gas to achieve the desired inlet concentration. The gas mixture was subsequently added to the reaction zone and the oxidation state of the metal was varied to establish its impact on reaction efficacy. The average residence time of the feed components in the reaction zone was about 4.1 seconds. The results are summarized below.

TABLE 4

| | Decreasing Relative Ionization Potential of Metal | | | |
|---|---|---|---|---|
| Metal | Temperature °C. | Feed | Sample # | Ethylene Yield (%) |
| Tin Base | 900 | n-hexane | 25 | 12.9 |
| " | " | " | 26 | 13.9 |
| " | " | " | 27 | 16.4 |
| " | " | " | 28 | 18.5 |
| " | " | " | 29 | 19.6 |

EQUIVALENTS

Those skilled in the art will recognize, or be able to ascertain using no more than routine experimentation, many equivalents of the invention described specifically herein. Such equivalents are intended to be encompassed in the scope of the following claims.

We claim:

1. A method for producing an alkene compound from an alkane component of an organic feed, comprising the steps of:

a) providing a reactor containing a molten metal bath, said molten metal bath including an elemental metal which can interact with an alkane component of the feed;

b) directing said feed into the molten metal bath at a rate which causes the elemental metal to interact with said alkane component; and c) establishing and maintaining operating conditions in said reactor to cause said elemental metal to interact with the alkane component, whereby at least one carbon-carbon double bond is formed in the alkane component to produce an alkene compound.

2. A method of claim 1 wherein the metal includes a transition metal.

3. A method of claim 2 wherein the reactor which is provided contains a molten metal bath including a transition metal that has an energy gap between its ground and first excited electronic states that is less than about 1.5 eV.

4. A method of claim 1 wherein the metal bath provided includes more than one metal.

5. A method of claim 4 wherein at least two of the metals of the molten metal bath provided include transition metals that have energy gaps between their ground and first excited electronic states of less than about 1.5 eV.

6. A method of claim 3 wherein the operating conditions established and maintained in the reactor include a temperature of the molten metal bath which is less than about 1,000° C.

7. A method of claim 3 wherein the operating conditions established and maintained in the reactor include a temperature of the molten metal bath which is less than about 2,000° C.

8. A method of claim 7 wherein the alkane component includes an aryl substituent.

9. A method of claim 8 wherein the alkane component includes butane, whereby the alkene compound that is discharged from the molten metal bath includes ethylene.

10. A method of claim 9 wherein the organic feed includes at least two alkane components.

11. A method of claim 10 wherein the operating conditions of said reactor include a concentration of dissolved carbon in the molten metal bath to be less than that of saturation.

12. A method of claim 1 wherein the feed further includes polymethyl methacrylate and wherein methyl methacrylate is formed.

13. A method of claim 1 wherein the feed includes at least one hydrogen-containing component.

14. A method of claim 1 wherein the metal is a component of the organic feed.

15. A method of claim 14 wherein the metal component is in an oxidized state.

16. A method of claim 14 wherein the metal component is in an anionic state.

17. A method of claim 1 wherein the molten metal bath provided includes at least two metals which can insert into the organic component of the feed.

18. A method of claim 14 wherein the metal of the molten metal bath is a metal anion formed by reduction of a metal component of the organic feed.

19. A method of claim 18 wherein the metal component of the organic feed is reduced in the molten metal bath by a metal component of said bath.

20. A method of claim 18 wherein the metal component of the organic feed is reduced in the molten metal bath by a carbon component of said bath.

21. A method of claim 1 wherein the metal which can interact with the alkane component of the feed is an alkaline metal.

22. A method of claim 1 wherein the metal which can interact with the alkane component of the feed is an alkaline earth metal.

23. A method of claim 14 wherein the metal of the molten metal bath is a metal cation formed by oxidation of a metal component of the organic feed.

24. A method of claim 23 wherein the metal of the metal component of the organic feed is oxidized in the molten metal bath by a metal component of said bath.

25. A method of claim 23 wherein the metal of the metal component of the organic waste feed is oxidized by halogenation in said bath.

26. A method of claim 25 wherein the metal is a metal ion.

27. A method of claim 26 wherein the metal ion is formed by an induction field.

28. A method of claim 26 wherein the metal ion is formed by a plasma gas.

29. A method for producing ethylene from a polyethylene terephthalate, comprising the steps of:

a) providing a reactor containing a molten metal bath, said molten metal bath including a metal which can interact with polyethylene terephthalate;

b) directing said polyethylene terephthalate into the molten metal bath at a rate which causes the metal to interact with said polyethylene terephthalate; and c) establishing and maintaining operating conditions in said reactor to cause said metal to interact with at least a portion of the polyethylene terephthalate, whereby at least one carbon-carbon double bond is formed in the polyethylene terephthalate to produce ethylene.

30. A method for producing a methyl methacrylate from polymethyl methacrylate, comprising the steps of:

a) providing a reactor containing a molten metal bath, said molten metal bath including a metal which can interact with the polymethyl methacrylate;

b) directing said polymethyl methacrylate into the molten metal bath at a rate which causes the metal to interact with said polymethyl methacrylate; and c) establishing and maintaining operating conditions in said reactor to cause said metal to interact with at least a portion of the polymethyl methacrylate, whereby at least one carbon-carbon double bond is formed in the polymethyl methacrylate to produce a methyl methacrylate.

31. A method for producing an alkene compound from an alkane component of an organic-containing feed, comprising the steps of:
   a) providing a reactor containing a molten metal bath including an elemental metal having an energy gap between its ground and first excited electronic states that can cause the elemental metal to be inserted into a sigma bond of an alkane component of the organic-containing feed;
   b) directing the organic-containing feed into the molten metal bath; and
   c) establishing and maintaining operating conditions in said reactor which cause the metal to insert into said sigma bond of said alkane component to form an organometallic intermediate by an oxidative addition reaction, and which cause the metal of the organometallic intermediate to be subsequently eliminated, whereby the organometallic intermediate is reformed to an alkene compound.

32. A method for producing an alkene compound from an alkane component of an organic-containing feed, comprising the steps of:
   a) providing a reactor containing a molten metal bath including an elemental metal having an energy gap between its ground and first excited electronic states of less than about 1.5 eV, whereby the metal can be inserted into a sigma bond of an alkane component of the organic-containing feed;
   b) directing the organic-containing feed into the molten metal bath; and
   c) establishing and maintaining operating conditions in said reactor which cause the metal to insert into said sigma bond of said alkane component to form an organometallic intermediate by an oxidative addition reaction, and which cause a metal-containing organic fragment to be subsequently eliminated from the organometallic intermediate, thereby causing a remaining fragment of the organometallic intermediate to be reformed to an alkene compound.

33. A method of claim 32 wherein the metal is in its oxidized state.

34. A method of claim 32 wherein the metal is a metal ion.

35. A method of claim 34 wherein the metal ion is formed by an induction field.

36. A method of claim 34 wherein the metal ion is formed by a plasma gas.

37. A method of claim 32 wherein the metal is in its anionic state.

38. A method of claim 32 wherein the molten metal bath includes more than one metal having an energy gap of less than about 1.5 eV.

39. A method of claim 32 wherein the metal is a transition metal.

40. A method of claim 32 wherein an anion of the metal is formed through reduction of the metal.

41. A method of claim 32 wherein an anion of the metal is formed through reduction of the metal by a second metal.

42. A method of claim 32 wherein an anion of the metal catalyst is formed through reduction of the metal by carbon.

43. A method of claim 32 wherein an alkaline metal is employed to produce an anion of the metal.

44. A method of claim 32 wherein an alkaline earth metal is employed to produce an anion of the metal.

45. A method of claim 32 wherein a cation of the metal is formed on oxidation of the metal.

46. A method of claim 32 wherein a cation of the metal is formed on oxidation of the metal by a second metal.

47. A method of claim 32 wherein a halide is employed to produce a cation of the metal.

48. A method for producing an unsaturated organic compound from an organic component of an organic feed, comprising the steps of:
   a) providing a reactor containing a molten rhodium-containing bath;
   b) directing said feed into the molten rhodium-containing bath at a rate which causes the rhodium to interact with said organic component; and
   c) establishing and maintaining operating conditions in said reactor to cause said rhodium to interact with the organic component, whereby at least one carbon-carbon double bond is formed in said portion of the organic component to produce an unsaturated organic compound.

49. A method for producing an unsaturated organic compound from an organic component of an organic feed, comprising the steps of:
   a) providing a reactor containing a molten copper-containing bath;
   b) directing said feed into the molten copper-containing bath at a rate which causes the copper to interact with said organic component; and
   c) establishing and maintaining operating conditions in said reactor to cause said copper to interact with the organic component, whereby at least one carbon-carbon double bond is formed in said organic component to produce an unsaturated organic compound.

50. A method for producing an unsaturated organic compound from a polyethylene terephthalate component of an organic feed, comprising the steps of:
   a) providing a reactor containing a molten metal bath, said molten metal bath including a metal which can interact with a polyethylene terephthalate component of the feed;
   b) directing said feed into the molten metal bath at a rate which causes the metal to interact with said polyethylene terephthalate component; and
   c) establishing and maintaining operating conditions in said reactor to cause said metal to interact with the organic component, whereby at least one carbon-carbon double bond is formed in said polyethylene terephthalate component to produce ethylene that is discharged from the molten metal bath.

51. A method for producing an unsaturated organic compound from a polyethylene terephthalate component of an organic feed, comprising the steps of:
   a) providing a reactor containing a molten metal bath, said molten metal bath including a metal which can interact with a polyethylene terephthalate component of the feed;
   b) directing said feed into the molten metal bath at a rate which causes the metal to interact with said polyethylene terephthalate component; and
   c) establishing and maintaining operating conditions in said reactor to cause said metal to interact with the polyethylene terephthalate component, whereby at least one carbon-carbon double bond is formed in said polyethylene terephthalate component to produce an aromatic compound that is discharged from the molten metal bath.

52. A method for producing an unsaturated organic compound from an organic containing feed, comprising the steps of:
   a) providing a reactor containing a molten metal bath including an elemental metal having an energy gap between its ground and first excited electronic states that can cause the elemental metal to be inserted into a sigma bond of an alkane component of the organic containing feed;
   b) directing the organic containing feed into the molten metal bath; and
   c) establishing and maintaining conditions in said reactor which causes the metal to insert into said sigma bond of said alkane component to form an organometallic intermediate by an oxidative addition reaction, and which causes a metal-containing alkane fragment to be subsequently eliminated from the organometallic intermediate, thereby causing a substantial portion of a remaining alkane fragment of the organometallic intermediate to be reformed to an unsaturated organic compound containing fewer carbon atoms.

53. A method of claim 52 where the metal interaction occurs at a carbon-carbon bond of said alkane component.

54. A method of claim 52 where the metal interaction occurs at a carbon-hydrogen bond of said alkane component.

55. A method for producing an unsaturated organic compound from an organic containing feed, comprising the steps of:
   a) providing a reactor containing a molten metal bath including an elemental metal having an energy gap between its ground and first excited electronic states of less than about 1.5 eV, whereby the metal can be inserted into a sigma bond of an alkane component of the organic containing feed;
   b) directing the organic containing feed into the molten metal bath; and
   c) establishing and maintaining conditions in said reactor which causes the metal to insert into said sigma bond of said alkane component to form an organometallic intermediate by an oxidative addition reaction, and which causes a metal containing alkane fragment to be subsequently eliminated from the organometallic intermediate, thereby causing a substantial portion of a remaining alkane fragment of the organometallic intermediate to be reformed to an unsaturated organic compound containing fewer carbon atoms.

56. A method of claim 55 where the metal interaction occurs at a carbon-carbon bond of said alkane component.

57. A method of claim 55 where the metal interaction occurs at a carbon-hydrogen bond of said alkane component.

58. A method for producing an unsaturated organic compound from a component of a hydrocarbon feed, said component containing only hydrogen and carbon, comprising the steps of:
   a) providing a reactor containing a molten metal bath, said molten metal bath including an elemental metal which can interact with an organic component of the feed;
   b) directing said feed into the molten metal bath at a rate which causes the elemental metal to interact with said hydrocarbon component; and
   c) establishing and maintaining conditions in said reactor to cause said elemental metal to interact with the hydrocarbon component, whereby at least one carbon-carbon double bond is formed in the organic component to produce an unsaturated organic compound.

59. A method of claim 58 where the metal interaction occurs at the carbon-carbon bond.

60. A method of claim 58 where the metal interaction occurs at the carbon-hydrogen bond.

61. A method for producing an unsaturated organic compound from an alkane portion of an organic component contained in an organic feed, comprising the steps of:
   a) providing a reactor containing a molten metal bath, said molten metal bath including an elemental metal which can interact to form an organometallic intermediate within the alkane portion of the organic component contained in said organic feed;
   b) directing said feed into the molten metal bath at a rate which causes said interaction; and
   c) establishing and maintaining conditions in said reactor to cause elimination of the interacted metal in its oxidized form from the alkane portion of the organic component contained in an organic feed, thereby producing predominately an organic compound containing a carbon-carbon double bond.

62. A method of claim 61 where the metal interaction occurs at a carbon-carbon bond of said alkane portion.

63. A method of claim 61 where the metal interaction occurs at a carbon-hydrogen bond of said alkane portion.

64. A method for producing an unsaturated organic compound from an organic component of an organic feed, comprising the steps of:
   a) providing a reactor containing a molten bath that includes a catalytic metal;
   b) directing said feed into the molten bath at a rate which causes the catalytic metal to interact with said organic component; and
   c) establishing and maintaining operating conditions in said reactor to cause said catalytic metal to interact with the organic component, whereby at least one carbon-carbon double bond is formed in said portion of the organic component to produce an unsaturated organic compound.

65. The method of claim 64, wherein said catalytic metal of the molten bath that is provided is rhodium.

66. The method of claim 64, wherein said catalytic metal of the molten bath that is provided is copper.

67. A method for producing an unsaturated organic compound from an organic component of an organic feed, comprising the steps of:
   a) providing a reactor containing a molten metal bath that includes an elemental metal component;
   b) directing said feed into the molten metal bath at a rate which causes the elemental metal to interact with said organic component; and
   c) establishing and maintaining operating conditions in said reactor to cause said elemental metal to interact with the organic component, whereby at least one carbon-carbon double bond is formed in said portion of the organic component to produce an unsaturated organic compound.

68. The method of claim 67, wherein the elemental metal is selected from the group consisting of elements having an atomic number of 39 through 46.

69. The method of claim 67, wherein the elemental metal is selected from the group consisting of elements having an atomic number of 21 through 29.

70. The method of claim 67, wherein the elemental metal is selected from the group consisting of elements in Group VIII of the Periodic Table of the Elements.

71. A method for producing ethylene from a polyethylene component of an organic feed, comprising the steps of:

a) providing a reactor containing a molten metal bath, said molten metal bath including a metal which can interact with a polyethylene component of the feed;

b) directing said feed into the molten metal bath at a rate which causes the metal to interact with said polyethylene component; and c) establishing and maintaining operating conditions in said reactor to cause said metal to interact with the polyethylene component, whereby at least one carbon-carbon double bond is formed in said polyethylene component to produce ethylene.

72. A method for producing an unsaturated organic compound from a plastic component of an organic feed, comprising the steps of:

a) providing a reactor containing a molten metal bath, said molten metal bath including a metal which can interact with a plastic component of the feed;

b) directing said feed into the molten metal bath at a rate which causes the metal to interact with said plastic component; and c) establishing and maintaining operating conditions in said reactor to cause said metal to interact with the plastic component, whereby at least one carbon-carbon bond is formed in the plastic component to produce an unsaturated organic compound.

* * * * *